United States Patent
Meineke et al.

(10) Patent No.: US 11,061,097 B2
(45) Date of Patent: Jul. 13, 2021

(54) DATA DRIVEN CORRECTION OF PHASE DEPENDING ARTEFACTS IN A MAGNETIC RESONANCE IMAGING SYSTEM

(71) Applicant: KONINKLIJKE PHILIPS N.V., Eindhoven (NL)

(72) Inventors: Jan Jakob Meineke, Hamburg (DE); Tim Nielsen, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 16/639,770

(22) PCT Filed: Aug. 15, 2018

(86) PCT No.: PCT/EP2018/072078
§ 371 (c)(1),
(2) Date: Feb. 18, 2020

(87) PCT Pub. No.: WO2019/038147
PCT Pub. Date: Feb. 28, 2019

(65) Prior Publication Data
US 2020/0209331 A1 Jul. 2, 2020

(30) Foreign Application Priority Data
Aug. 22, 2017 (EP) .................................. 17187235

(51) Int. Cl.
*G01R 33/565* (2006.01)
*A61B 5/055* (2006.01)
(Continued)

(52) U.S. Cl.
CPC ............ *G01R 33/565* (2013.01); *A61B 5/055* (2013.01); *G01R 33/3635* (2013.01); *G01R 33/5611* (2013.01)

(58) Field of Classification Search
CPC ............ G01R 33/3635; G01R 33/5611; G01R 33/565; A61B 5/055
See application file for complete search history.

(56) References Cited

U.S. PATENT DOCUMENTS

| 5,759,152 A |   | 6/1998 | Felmlee et al. |
| 5,929,638 A | * | 7/1999 | Aldefeld .......... G01R 33/56518 324/307 |

(Continued)

OTHER PUBLICATIONS

Pruessmann et al "Sense: Sensitivity Encoding for Fast MRI" Magnetic Resonance in Med. vol. 42 p. 952-962 (1999).
(Continued)

*Primary Examiner* — Gregory H Curran

(57) ABSTRACT

The invention provides for an MRI system (100) with an RF system for acquiring magnetic resonance data (142). The RF system comprises a set of antenna elements (126). The MRI system (100) further comprises a processor for controlling the MRI system (100). Magnetic resonance data is acquired. Combined image data (144) is reconstructed. The reconstruction comprises transforming the acquired magnetic resonance data (142) from k-space to image space and combining the resulting image data. For each antenna element (126) magnetic resonance data (146) is simulated using the reconstructed combined image data (144). The simulation comprises transforming the reconstructed combined image data (144) from image space to k-space. A phase correction factor is determined, The determination comprises calculating phase differences between the acquired magnetic resonance data (142) and the simulated magnetic resonance data (146). The acquired magnetic resonance data (142) is corrected using the phase correction factor. In this way, the invention allows for correcting phase errors caused e.g. by subject motion such as respiration by B0 off-resonances, etc.

14 Claims, 4 Drawing Sheets

(51) Int. Cl.
*G01R 33/36* (2006.01)
*G01R 33/561* (2006.01)

(56) References Cited

U.S. PATENT DOCUMENTS

2007/0182411 A1* 8/2007 Bammer .......... G01R 33/56341
324/307
2012/0319686 A1 12/2012 Jesmanowicz et al.
2019/0369192 A1* 12/2019 McKay ............ G01R 33/56554

OTHER PUBLICATIONS

Bernstein et al "Handbook of MRI Pulse Sequqnces" p. 527-531 (2004).
International Search Report From PCT/EP2018/072078 dated Dec. 5, 2018.
DJ Larkman et al: "Consistency Based Ghost Busting(CBGB)",Proceedings of the International Society for Magnetic Resonance in Medicine, ISMRM,Joint Annual Meeting ISMRM-ESMRMB, Berlin,Germany, May 19-25, 2007, May 5, 2007 (May 5, 2007), p. 987.
Stefan Skare et al:"An auto-calibrated, angularly continuous, two-dimensional GRAPPA kernel for propeller trajectories", Magnetic Resonance in Medicine, vol. 60, No. 6, Nov. 24, 2008 (Nov. 24, 2008), pp. 1457-1465.
Alexy A. Samsonov et al: "POCS-enhanced correction of motion artifacts in parallel MRI", Magnetic Resonance in Medicine, vol. 63, No. 4, Apr. 1, 2010 (Apr. 1, 2010),pp. 1104-1110.

\* cited by examiner

US 11,061,097 B2

DATA DRIVEN CORRECTION OF PHASE DEPENDING ARTEFACTS IN A MAGNETIC RESONANCE IMAGING SYSTEM

CROSS REFERENCE TO RELATED APPLICATIONS

This application is a U.S. national phase application of International Application No. PCT/EP2018/072078 filed on Aug. 15, 2018, which claims the benefit of EP Application Serial No. 17187235.1 filed on Aug. 22, 2017 and is incorporated herein by reference.

FIELD OF THE INVENTION

The invention relates to phase correction in magnetic resonance imaging, in particular it relates to methods and apparatuses for phase correction in a magnetic resonance imaging system using multiple antenna elements.

BACKGROUND OF THE INVENTION

In magnetic resonance imaging (MRI), phase variations due to spatio-temporal inhomogeneities of the main magnetic field are a common problem. Image artefacts, like e.g. ripples and intensity modulations, which are caused by these fluctuations can significantly reduce the quality of the images.

Such inhomogeneities are for example due to subject motion which is an ubiquitous problem in MRI. But even when the subject is completely still within a field of view, drifts or fluctuations, whether they are of physiologic, e.g. breathing or cardiac motion, or technical origin, e.g. thermal drifts of the scanner, can have a significant impact on image quality.

This is e.g. particularly relevant for gradient-echo scans with long TE, where drifts and fluctuations of the main filed, i.e. the $B_0$-off-resonance field, can lead to ghosting and other artefacts. To correct for these errors a variety of methods have been proposed in the past, ranging from the use of additional magnetic resonance signals, e.g. navigators or navigator echoes, over external sensors such as respiratory belts or cameras, to retrospective approaches involving iterative reconstruction while minimizing a given image cost-function.

SUMMARY OF THE INVENTION

The invention provides for a magnetic resonance imaging system, a method of operating the magnetic resonance imaging system, and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by nuclear spins using the antenna of a Magnetic resonance apparatus during a magnetic resonance imaging scan. MRF magnetic resonance data is magnetic resonance data. Magnetic resonance data is an example of medical image data. A Magnetic Resonance Imaging (MRI) image or MR image is defined herein as being the reconstructed two or three-dimensional visualization of anatomic data contained within the magnetic resonance imaging data. This visualization can be performed using a computer.

In one aspect, the invention provides for a magnetic resonance imaging system. The MRI system comprises a main magnet for generating a main magnetic field, i.e. a B0-off-resonance field, within an imaging zone as well as a magnetic field gradient system for generating a spatially dependent gradient magnetic field within the imaging zone. The MRI system comprises a radio-frequency system with a set of antenna elements each configured for acquiring magnetic resonance data from the imaging zone. The set of antenna elements may e.g. be provided in form of a magnetic resonance imaging coil which comprises multiple antenna elements, i.e. a multi-element magnetic resonance imaging coil. The coil functions a receiving coil for performing magnetic resonance imaging, i.e. the antenna elements may function as receiving coil elements.

A memory of the MRI system stores machine executable instructions and pulse sequence commands. The pulse sequence commands are configured for controlling the MRI system to acquire the magnetic resonance data from the imaging zone. For example, the pulse sequence commands may be configured for controlling the magnetic resonance imaging system to acquire the magnetic resonance data according to a parallel imaging protocol. The pulse sequence data may for instance be provided in form of commands which may be executed by a processor or it may be provided in form of a timing diagram or timing information which may be converted by a program into commands for controlling the magnetic resonance imaging system. Furthermore, a processor is provided for controlling the magnetic resonance imaging system. An execution of the machine executable instructions causes the processor to control the MRI system to perform the following:

Magnetic resonance data is acquired from the imaging zone by each of the antenna elements. The acquired magnetic resonance data is used to reconstruct combined image data. The reconstruction comprises transforming the acquired magnetic resonance data of the antenna elements from k-space to image space, e.g. using inverse Fourier transformation. Then, the resulting image data of the antenna elements is combined.

The image data of the antenna elements may be combined by any suitable method appropriate for the chosen sampling scheme, for example sum-of-squares, SENSE, etc.

The reconstructed combined image data is used to simulate magnetic resonance data acquired by each antenna element. This simulation comprises transforming the reconstructed combined image data from image space to k-space, for each antenna element, e.g. using Fourier transformation.

Transformation from image space to k-space may be performed using Fourier transformation, while transformation from k-space to image space may be performed using inverse Fourier transformation.

For each antenna element, a phase correction factor for the acquired magnetic resonance data of the respective antenna element is determined using the acquired as well as the simulated magnetic resonance data. For this purpose, phase differences are calculated between the acquired magnetic resonance data, or a suitable combination of the acquired data, e.g. average over dynamics, and the simulated magnetic resonance data of the respective antenna element.

The acquired magnetic resonance data of each element is corrected using the phase correction factor determined for the respective antenna element.

The invention provides a magnetic resonance imaging system which may enabled to correct for drifts and fluctuations in the $B_0$-off-resonance field during an MRI scan from the complex raw data, i.e. the acquired MRI data in k-space, without any additional information, e.g. from an optical camera, breathing belt, or MR navigator etc. Main magnetic field fluctuations are rather estimated form the raw MRI k-space data, i.e. a data-driven approach is used. Such a data-driven eastimation of field fluctuations may overcome the need for additional sensors, additional MR data acquisitions (navigators) as well as solutions for complicated minimization problems.

The mechanism behind the correction is that the combination of magnetic resonance data from different channels, i.e. antenna elements, in the image domain and mapping this combined data back to k-space effectively mixed information from neighboring k-space points which may e.g. result in an averaging. The resulting averaged data, also refered to as simulated magnetic resonances data herein, has a lower phase error because not all neighboring k-space points have experienced the same phase error during data acquisition. Thus, averaging may at least partly cancel phase errors comprised by the acquired magnetic resonance data.

This may enable correcting image artefacts caused by $B_0$-off-resonance field fluctuations, which may particularly be relevant for gradient-echo scans with long TE, such as for T2*-mapping, susceptibility weighted imaging or quantitative susceptibility mapping.

Sources of temporal field fluctuations of the main magnetic field may e.g. be caused by a main magnetic field drift of the main magnet during scanning, e.g. due to heating. A further source may e.g. be a breathing motion of the subject in the imaging zone or cardiac motion. Cardiac motion may be particular relevant in e.g. dynamic contrast enhanced (DCE) breast imaging, where the heart is close to the region of interest. Also, for field changes due to gross patient motion outside of the imaged field of view the proposed approach for a data-driven correction may be useful.

Embodiments may for example be used for artifact reduction for 3D Cartesian gradient echo scans, but may e.g. also be applied to multi-slice 2D scans. Other applications for the technique may e.g. be dynamic scans. The phase correction factor may be calculated using a single frames or an temporal average of all dynamic frames. The latter has the advantage that the SNR is improved.

According to embodiments, multiple acquisitions of magnetic resonance data of the same k-space lines may be executed. SNR of a final magnetic resonance image may be improved by acquirng some or all k-space lines multiple times and average them. The phase correction may be applied to the acquired magnetic resonance data e.g. before averaging over repetitions in order to remove the effect of the $B_0$-fluctuations.

Echo planar imaging is a technique which enables very fast imaging, but the k-space is assembled from multiple gradient echoes acquired at different echo times. Thus, off-resonance effects may accumulate during the echo train. Here, the correction provided by the proposed magnetic resonace imaging system may as well be applied taking into account the actual echo time of each k-space line.

The correction may also be applied to dynamic, single-shot EPI scans if the time average is taken as a common reference. This may e.g. be important for functional MRI, where single-shot EPI is the standard sequence and reliable signal intensity of T2* weighted images is a key factor in the quantification of the BOLD effect.

According to embodiments, a single coil magnetic resonance image may be reconstructed for each antenna element, which may e.g. be implemented in form of receiver coils, using the magnetic resonance data acquired by the respective antenna element. From the single coil images, a combined magnetic resonance image may be formed e.g. as a weighted combination of the single coil images. Each of the single coil images may be weighted by a coil sensitivity of the receiver coil which has acquired the magnetic resonance data used to reconstruct the respective single coil image. For each of the receiver coils simulated magnetic resonance data may be calculated, e.g. by back-transforming the combined magnetic resonance image weighted by the coil sensitivity of the respective coil. Phase deviates between the acquired MRI data and the simulated MRI data may be derived by comparing, e.g. taking the ratio, of the back-transformed k-space magnetic resonance data to the acquired, i.e. measured, magnetic resonance k-space magnetic resonance data.

Thus, phase variations of the main magnetic field are computed from measured magnetic resonance signals from individual receiver coils. Therein, from a combined image, that is formed as a weighted superposition of several images reconstructed from data measured by the receiver coils, synthesized, i.e. simulated, k-space data for each of the respective reveiver coils is back-transformed. The combined image may provide a good approximation of the actual magnetization distribution in a subject to be examined in the imaging zone assuming Gaussian distributed noise.

Embodiments may benefially be integrated in methods for parallel imaging. As used herein a parallel imaging method encompasses imaging methods using a plurality of antenna elements, e.g. receiving coils, for magnetic resonance imaging. Spatial information obtained from an array of antenna elements sampling data in parallel may be used to perform some portion of spatial encoding usually done by gradient fields, typically the phase encoding gradient. Thus, MRI acquisition times may be speeded up without a need for faster switching gradients or for additional RF power deposited. Furthermore, parallel imaging may be used to disentangle magnetic resonance signals originating from different spatial locations. Examples of parallel imaging methods are k-space simultaneous acquisition of spatial harmonics (SMASH), generalized autocalibrating partially parallel acquisitions (GRAPPA), and image domain sensitivity encoding (SENSE).

The SENSE reconstruction technique was introduced by the journal article Pruessmann et al., "SENSE: sensitivity encoding for fast MRI," Magnetic Resonance in Medicine, 42:952-962 (1999). The terminology to describe the SENSE reconstruction is well known and has been the subject of many review articles and is present in standard texts on Magnetic Resonance Imaging. For example, "Handbook of MRI Pulse Sequences" by Bernstein et. al., published by Elsevier Academic Press in 2004 contains a review of the SENSE reconstruction technique on pages 527 to 531.

According to embodiments, the reconstruction of combined image data, the simulation of magnetic resonance data, the determination of the phase correction factor and the correction of the acquired magnetic resonance data are iteratively repeated using the corrected magnetic resonance data in order to further correct the corrected magnetic resonance data until a predefined termination criterion is satisfied. The predefined termination criterion may for example be satified, when the calculated phase difference becomes smaller than a predefined threshold or when a predefined maximum number of iteration steps is reached.

Embodiments may have the beneficial effect of providing an accurate and fast way of fully mapping spatial inhomogeneities of the main magnetic field in a magnetic resonance imaging system, i.e. $B_0$-mapping. Iteration may eliminate phase variations due other causes and isolates the phase variations due to spatial variations of the main magnetic field. The drift of the $B_0$-off-resonance frequency may thus be deduced from the raw magnetic resonance signal itself in an iterative process which improves the self-consistency of the data set. A small number of iteration steps, for example 3 to 10, like e.g. 4, 5, 6, or 7, may be sufficient to fully remove artefacts due to temporal inhomogeneities, i.e. effects of temporal variations.

If the measured MR signal is perturbed by a contribution which changes in time, this leads to inconsistencies in the Fourier-space data. Going full cycle from acquired magnetic resonace data in k-space to reconstructed combined image data in image space and back to the raw data, these inconsistencies lead to a residual phase error in k-space. This error is proportional, but potentially smaller, than the actual phase error caused by the fluctuating $B_0$-off-resonance field. The full, actual phase error may be obtained by iterating the computation. The iteration depending on the details of the image reconstruction method used may e.g. be performed as follows:

1. Given the measured complex magnetic resonance signal $\rho(\alpha)$ in k-space for a number of antenna elements indexed by $\alpha$, images for each of the antenna elements may be reconstructed using an inverse Fourier transformation for transforming the data from k-space k to image space r:

$I(r, \alpha) = F^{-1}(\rho(k, \alpha))$.

2. Subsequently, the images of the individual antenna elements are for example combined using the sensitivities s($\alpha$) of the respective antenna elements, i.e. receiving coils:

$$I = \frac{\Sigma_\alpha s^*(\alpha) I(\alpha)}{\Sigma_\alpha s^*(\alpha) s(\alpha)}.$$

The coil-sensitivities of the individual receiving coils, i.e. antenna elements, may e.g. be known from reference scans or from auto-calibration.

The resulting combined image I would normally be the end-point of the reconstruction.

3. Here, however the combined image I is used to simulate magnetic resonance data acquired by each of the antenna elements. The image I is e.g. multiplyed by the coil-sensitivity of the antenna element, for which the magnetic resonance data is to simulated, and the Fourier transformed from image space back to k-space obtain $\rho'_\alpha$, the simulated k-space data for antenna element $\alpha$:

$\rho'(k, \alpha) = F(s(\alpha) I)$.

4. The phase error $\phi_0(\alpha)$ is given by the phase of the complex ratio of $\rho'(\alpha)$ and $\rho(\alpha)$. The data may be sorted according to the time in which k-space was traversed and low pass filtered in order to improve SNR. The phase correction factor $\phi_0(\alpha)$ is then applied to the raw data $\rho(\alpha)$ and the next iteration is started. After a few iterations, the process converges yielding the total phase correction.

The fact that there is a difference in $\rho(\alpha)$ and $\rho'(\alpha)$ at all, can be understood by considering that the multiplication with the coil-sensitivity in images space corresponds to a convolution with the Fourier transform in k-space. This mixes the inconsistencies induced by the changing $B_0$-off-resonance field, leading on an averaging of the inconsistencies. The procedure above can be iterated until the inconsistency has vanished, e.g. after 3, 4, 5, 6 or 7 iterations.

The insight that the effect of coil-combination leads to difference in the original and simulated k-space data allows to detect $B_0$ fluctuations on a data-driven basis.

Steps 1 and 2 above describe a multi-channel reconstruction for e.g. a fully sampled Cartesian data sets. In more general terms, they describe a way from multi-channel k-space data to a single reconstructed image (e.g. 2D, 3D or 2D+time, etc), i.e. they describe an image reconstruction algorithm. Depending on the specifics of the data acquisition, e.g. under-sampling of k-space, or half-scan, the actual form of the image reconstruction may differ from the examplary formulas in 1 and 2 above.

Step 3 describes a simulation data in k-space from an image, i.e. data in image space. Again, the mathematical details of this step depend on the specifics of the acquisition.

Independently of the details of the reconstruction of the combined image data in image space, the phase correction may e.g. be calculated iteratively as follows: Let $\rho_0$ ($k_x$, $k_y$, $k_z$, $\alpha$) be the acquired magnetic resonance data of antenna element $\alpha$ in k-space and $\rho'_0$ ($k_x$, $k_y$, $k_z$, $\alpha$) the magnetic resonance data in k-space simulated from $\rho_0$, where $k_{x,y,z}$ is the position in k-space and $\alpha$ is the antenna element, i.e. channel, index.

Using $\rho_0$ ($k_x$, $k_y$, $k_z$, $\alpha$) and $\rho'_0$ ($k_x$, $k_y$, $k_z$, $\alpha$) a first phase correction factor $\phi_0$ ($\alpha$) is calculated:

$$\phi_0\ (k_x,\ k_y,\ k_z,\ \alpha)=\text{angle}[\rho_0\ (k_x,\ k_y,\ k_z,\ \alpha)/\ \rho'_0\ (k_x,\ k_y, k_z,\ \alpha)]$$

The phase correction factor $\phi_0$ ($\alpha$) is used to correct the acquired magnetic resonace data $\rho_0$ ($k_x$, $k_y$, $k_z$, $\alpha$) resulting in the corrected magnetic resonance data $\rho_1$ ($k_x$, $k_y$, $k_z$, $\alpha$):

$$\rho_1\ (k_x,\ k_y,\ k_z,\ \alpha)=\rho_0\ (k_x,\ k_y,\ k_z,\ \alpha)*\exp\ (-i\phi_0(k_x,\ k_y, k_z,\ \alpha))$$

Then further data $\rho'_1$ ($k_x$, $k_y$, $k_z$, $\alpha$) is simulated starting from the corrected magnetic resonance data $\rho_1$ ($k_x$, $k_y$, $k_z$, $\alpha$) instead of the originally acquired magnetic resonance data $\rho_0$ ($k_x$, $k_y$, $k_z$, $\alpha$). The data $\rho_1$ ($k_x$, $k_y$, $k_z$, $\alpha$) and $\rho'_1$ ($k_x$, $k_y$, $k_z$, $\alpha$) are then used to compute a further phase correction $\phi_1$ and so on until a predefined termination criterion is satisfied. The predefined criterion may for example be satified, when a phase correction $\phi_n$ is reached which is smaller than a predefined threshold $\phi_t$ or when a predefined maximum number of iteration steps n is reached.

The aforementioned iteration may converge after a few steps. The total phase correction is the sum of all $\phi_i$ ($k_x$, $k_y$, $k_z$, $\alpha$), i.e. $\Sigma_{i=1}^{n_{con}} \phi_i$, wherein $n_{con}$ is the number of steps after which the iteration converges, i.e. phase correction $\phi_n$ is smaller than a predefined threshold $\phi_t$.

Please note, as an alternative to the ratio of $\rho_i$ and $\rho'_i$ which is used above, the product of $\rho_i$ and $\rho'_i$ may be used in order to calculate the phase correction factor. Here, $\rho'^*_i$ is the complex conjugate of $\rho'_i$.

According to embodiments, each antenna element acquires multiple sets of magnetic resonance data from the imaging zone. Each one of the sets is acquired at a different time. In other words, each antenna element may acquire a first set of magnetic resonance data at a first time, a second set of magnetic resonance data at a second time and so on. The transformation of the acquired magnetic resonance data of the antenna elements from k-space to image space comprises for each antenna element averaging the acquired magnetic resonance data of the sets of the respective antenna element over time and transforming the resulting magnetic resonance data from k-space to image space. Or for each antenna element the magnetic resonance data of the sets of the respective antenna element may be transformed and the resulting magnetic resonance data is averaged over time.

Embodiments may have the beneficial effect of enabling a compensation of fluctuations in case of time series measurements, where multiple sets of magnetic resonance data are acquired at multiple times. This may be beneficial for DCE-MRI oder fMRI/EPI, where data is measured in 2D +time.

According to embodiments, for each point in k-space comprised by the acquired magnetic resonance data an individual phase correction factor is determined and used for the correction of the magnetic resonance data acquired for the respective point. The determination of the individual phase correction factors comprises calculating for each of the points in k-space an individual phase difference between the magnetic resonance data acquired for the respective point and the magnetic resonance data simulated for the respective point.

Embodiments may have the beneficial effect of for each point in k-space an individual phase correction factor may be determined allowing for a precise phase correction of individual frequencies.

According to embodiments, the phase correction factor is an averaged phase correction factor determined for a subset of the acquired magnetic resonance data and used for the correction of the acquired magnetic resonance data comprised by the subset. The determination of the averaged phase correction factor comprises calculating an averaged phase difference by averaging over the phase differences calculated between the acquired magnetic resonance data comprised by the subset and the simulated magnetic resonance data.

Embodiments may have the beneficial effect depending on the selection of the subset and the details of the averaging procedure used, different ways of balancing the spatial resolution and SNR of the correction may be implemented. For example, points with high signal may contribute more to the final average than points with low signal resulting in an SNR weighted averaging According to embodiments, the subset comprises a first data selection of the acquired magnetic resonance data which is located on a line along a read-out direction in k-space such that the averaged phase difference is averaged over the read-out direction. The read-out direction may be positioned along the direction $k_x$, and the phase correction factor may be calculated as follows:

$$\phi_i\ (k_x,\ k_y,\ k_z,\ \alpha)=\text{angle}\ [\text{mean}_{k_x}\ (\rho_i\ (k_x,\ k_y,\ k_z,\ \alpha)/\rho'_i\ (k_x,\ k_y,\ k_z,\ \alpha))]$$

or $$\phi_i(k_x,\ k_y,\ k_z,\ \alpha)=\text{angle}\ [\text{mean}_{k_x}\ (\rho_i(k_x,\ k_y,\ k_z,\ \alpha)*\rho'^*_i (k_x,\ k_y,\ k_z,\ \alpha))]$$

According to embodiments, the subset comprises a second data selection of the acquired magnetic resonance data of different ones of the antenna elements acquired for the same point in k-space such that the averaged phase difference is averaged over antenna elements. The phase correction factor may be calculated as follows:

$$\phi_i\ (k_x,\ k_y,\ k_z,\ \alpha)=\text{angle}\ [\text{mean}_\alpha(\rho_i(k_x,\ k_y,\ k_z,\ \alpha)/\rho p'_i (k_x,\ k_y,\ k_z,\ \alpha))]$$

or $$\phi_i\ (k_x,\ k_y,\ k_z,\ \alpha)=\text{angle}\ [\text{mean}_\alpha(\rho_i(k_x,\ k_y,\ k_z,\ \alpha)*\rho'^*_i (k_x,\ k_y,\ k_z,\ \alpha))]$$

According to embodiments, the subset comprises a third data selection of the acquired magnetic resonance data which is acquired within a predefined time window such that the averaged phase difference is averaged over the time window. The phase correction factor may be calculated as follows:

$$\phi_i\ (k_x,\ k_y,\ k_z,\ \alpha)=\text{angle}\ [\text{mean}\ (\rho_i(k'_x,\ k'_y,\ k'_z,\ \alpha)/\rho'_i (k'_x,\ k'_y,\ k'_z,\ \alpha))]$$

or $$\phi_i\ (k_x,\ k_y,\ k_z,\ \alpha)=\text{angle}\ [\text{mean}\ (\rho_i(k'_x,\ k'_y,\ k'_z,\ \alpha)*\rho'^*_i (k'_x,\ k'_y,\ k'_z,\ \alpha))].$$

The averaging operation includes all k-space points $k'_{x,y,z}$ which are acquired within a certain time-window around the acquisition time of $k_{x,y,z}$.

According to embodiments, weighting factors are assigned to the acquired magnetic resonance data comprised by the subset and used for calculating the averaged phase difference. For example, hard weights of 0 or 1 may be used. Such hard weights correspond to a selection of a subset as described above, where all the magnetic resonance data comprised by the subset is weighted equally, while all the magnetic resonance data is neglected for the averaging. Alternatively, a plurality of different discrete weighting factors may be introduced. These may e.g. be uniformly distributed over the interval [0;1] or according to a continues function, e.g. according to a Gaussian distribution. Thus, different data points of the magnetic resonance data may be weighted differently depending e.g. on their position in k-space, on their time of acquisition, on the antenna element by which it has been acquired, etc.

According to embodiments, the transformation of the reconstructed combined image data from image space to k-space is performed for each dimension of image-space.

Embodiments may have the beneficial effect that the phase error averaging effect describe above is implemented for all k-space dimensions.

According to embodiments, the transformation of the reconstructed combined image data from image space to k-space is performed for each dimension of image-space except for a subset of dimensions of image space which is kept untransformed such that the resulting simulated magnetic resonance data is located in a hybrid space comprising the subset of dimensions of image space and one or more k-space dimensions. For the determination of the phase correction factor and the correction of the acquired magnetic resonance data a transformation of the acquired magnetic resonance data of each antenna element from k-space to image space is performed for the dimensions of image space comprised by the subset of dimensions such that the resulting transformed acquired magnetic resonance data is located in the hybrid space and the determination of the phase correction factor and the correction of the acquired magnetic resonance data are performed in the hybrid space using the transformed acquired magnetic resonance data. For example, the subset of dimensions of image space comprises one dimension of image space, the respective dimension e.g. coinciding with the read-out direction. According to another example, the subset of dimensions of image space comprises multiple dimensions of image space.

Embodiments may have the beneficial effect that instead of computing the phase correction factor in pure k-space, the phase correction factor is computed in a hybrid space x, $k_y$, $k_z$, where the inverse Fourier-transform has been carried out e.g. in readout direction. This may have the advantage that the spatial information in x-direction may be directly used in the calculation of the phase correction. If there is e.g. a reason to believe that the $B_0$ fluctuations may vary spatially, the readout direction can be positioned along the direction of the strongest variation and the correction calculation carried out in hybrid space. Spatial smoothing along x may be used to improve SNR analogous to averaging over $k_x$ as described above. Using the hybrid space may e.g. for a Cartesian magnetic resonance data acquisitions.

According to embodiments, an interlaced sampling scheme in k-space is used for the acquisition of the magnetic resonance data, wherein according to the interlaced sampling scheme magnetic resonance data from neighboring points in k-space comprised by the acquired magnetic resonance data is not acquired in direct succession.

Embodiments may have the beneficial effect that the sampling of k-space may be optimized in order to maximize the "averaging" effect of the convolution with the Fourier-transform described above. Thus, the error reduction may become more effective. Magnetic resonance data acquired close in time from neighboring k-space points may experience almost the same phase error. Thus, by avoid acquiring magnetic resonance data from neighboring k-space points close in time, the averaging effect described above due to combining magnetic resonance data from different antenna elements in the image domain and mapping the combined data back to k-space may be more effective, because data acquired at almost the same time may experience almost the same phase error and thus reduce the averaging effect which is based on different phase error experienced by the k-space points during acquisition.

According to embodiments, the distance between points in k-space for which magnetic resonance data is acquired in direct succession is at least as large as an effective antenna element footprint in k-space.

Embodiments may have the beneficial effect that they may guarantee an efficient error reduction. The effective antenna element footprint in k-space may depends on the parallel imaging capability of the employed coil array which may thus be taken into account.

In another aspect, the invention provides invention a computer program product comprising machine executable instructions for execution by a processor controlling a magnetic resonance imaging system. The magnetic resonance imaging system comprises a main magnet for generating a main magnetic field within an imaging zone, a magnetic field gradient system for generating a spatially dependent gradient magnetic field within the imaging zone, and a radio-frequency system comprising a plurality of antenna elements each configured for acquiring magnetic resonance data from the imaging zone. The magnetic resonance imaging system may further comprise a memory for storing machine executable instructions and pulse sequence commands, wherein the pulse sequence commands are configured for controlling the magnetic resonance imaging system to acquire the magnetic resonance data from the imaging zone.

An execution of the machine executable instructions causes the processor to control the magnetic resonance imaging system to acquire magnetic resonance data from the imaging zone by each of the antenna elements. The MRI system reconstructs combined image data. The reconstruction comprises transforming the acquired magnetic resonance data of the antenna elements from k-space to image space, e.g. using inverse Fourier transformation, and combining the resulting image data of the antenna elements. Magnetic resonance data acquired by each antenna element is simulated using the reconstructed combined image data. The simulation comprises transforming the reconstructed combined image data from image space to k-space, e.g. using Fourier transformation.

For each antenna element the MRI system determines a phase correction factor for the acquired magnetic resonance data of the respective antenna element. The determination comprises calculating phase differences between the acquired magnetic resonance data and the simulated magnetic resonance data of the respective antenna element. The acquired magnetic resonance data of each respective antenna element is then corrected using the phase correction factor determined for the respective antenna element.

In another aspect, the invention provides a method of operating a magnetic resonance imaging system as described above. The method comprises acquiring magnetic resonance data from the imaging zone by each of the antenna elements. Combined image data is reconstructed. The reconstruction comprises transforming the acquired magnetic resonance data of the antenna elements from k-space to image space, e.g. using inverse Fourier transformation, and combining the resulting image data of the antenna elements.

Magnetic resonance data acquired by each antenna element is simulated using the reconstructed combined image data. The simulation comprises transforming the reconstructed combined image data from image space to k-space, e.g. using Fourier transformation.

For each antenna element a phase correction factor is determined for the acquired magnetic resonance data of the respective antenna element. The determination comprises calculating phase differences between the acquired magnetic resonance data and the simulated magnetic resonance data of the respective antenna element. Finally, the acquired magnetic resonance data of each antenna element is corrected using the phase correction factor determined for the respective antenna element.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
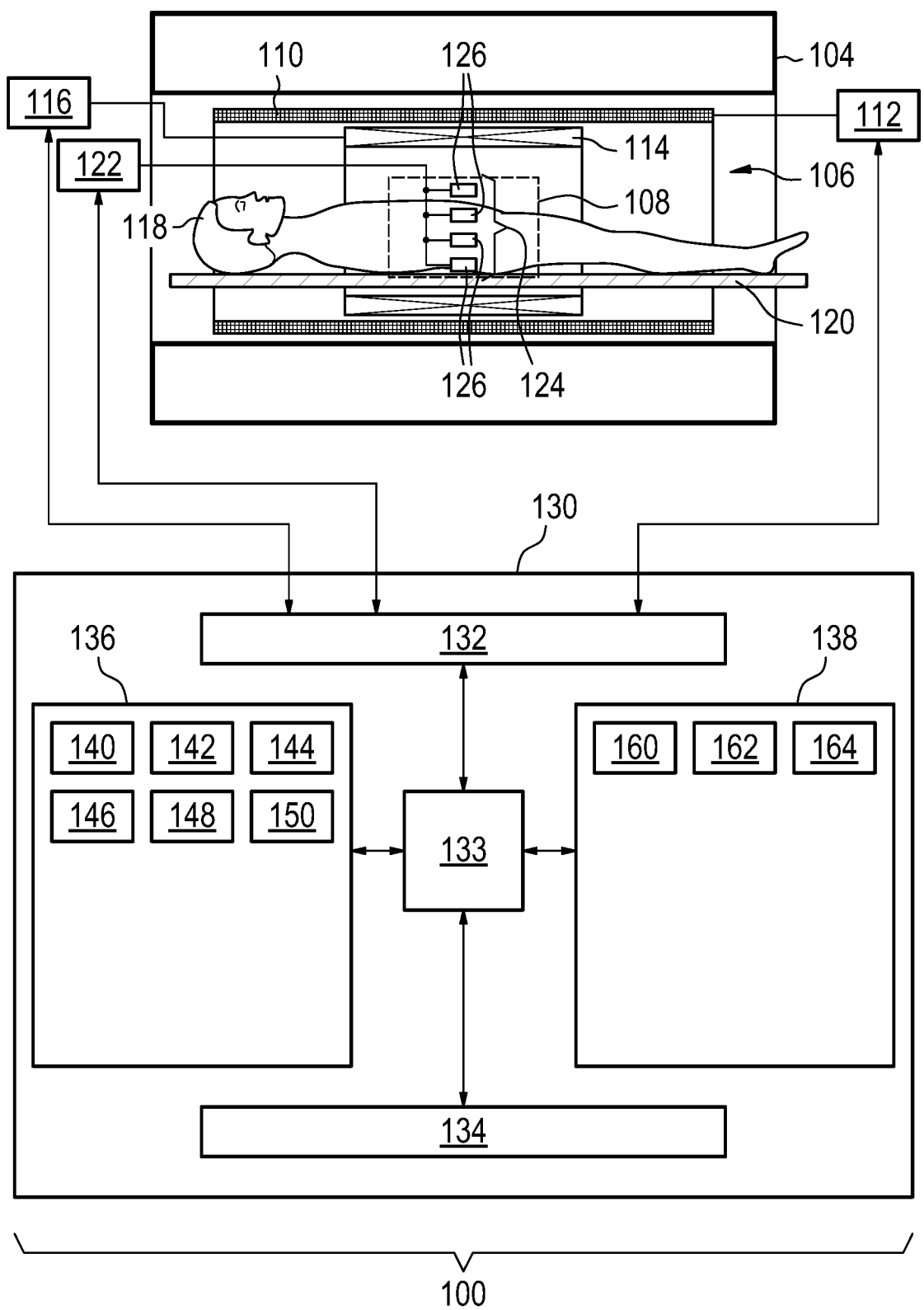
FIG. 1 illustrates an example of a magnetic resonance imaging system.

FIG. 1 shows an example of a magnetic resonance imaging system 100. The magnetic resonance imaging system 100 comprises a main magnet 104. The magnet 104 is a superconducting cylindrical type magnet 104 with a bore 106 through it. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Within the bore 106 of the magnet 104 is a body coil 114. The body coil 114 may be e.g. be a quadrature body coil (QBC) or a whole-body coil. The body coil 114 is shown as being connected to a transceiver 116. In some embodiments body coil 114 may be a whole-body coil and connected to a whole-body coil radio frequency amplifier and/or receiver, however this is not shown in this example. If both a transmitter and a receiver 116 are connected to the whole-body coil 114, a means for switching between the transmit and receive mode may be provided. For example, a circuit with a pin diode may be used to select the transmit or receive mode. A subject support 120 supports a subject 118 within the imaging zone.

A transceiver 122 is shown as being connected to a radio-frequency system comprising a magnetic resonance imaging coil 124. In this example, the magnetic resonance imaging coil 124 is a surface coil comprising multiple antenna elements 126. The transceiver 122 is operable for sending and receiving individual RF signals to the individual antenna elements 126. In this example, the transceiver 116 and the transceiver 122 are shown as being separate units. However, in other examples the units 116 and 122 could be combined.

The transceiver 116, the transceiver 122, and the magnetic field gradient coil power supply 112 are shown as being connected to a hardware interface 132 of a computer 130. The computer 130 is further shown as containing a processor 133 which is operable for executing the machine-readable instructions. The computer 130 is further shown as comprising a user interface 134, computer storage 136 and computer memory 138 which are all accessible and connected to the processor 133.

The computer storage 136 is shown as containing one of more pulse sequences 140. The pulse sequences 140 are either instructions or data which can be converted into instructions which enable the processor 133 to acquire magnetic resonance data using the magnetic resonance imaging system 100.

The computer storage is further shown as containing magnetic resonance data 142 acquired by the antenna elements 126. The computer storage is further shown as containing reconstructed combined image data 144. The reconstructed combined image data 144 is calculated using the acquired magnetic resonance data 142. This may be performed using several different techniques. It may e.g. be done using the SENSE protocol.

The computer storage 136 is further shown as containing simulated magnetic resonance data 146 simulated using the reconstructed combined image data 144. Depending on the technique used for reconstructing data 144 in image space and simulating data 146 a set of coil sensitivities of the set antenna elements 126 may be provided by the computer storage 136 as well.

The computer storage may further comprise a definition of a set of points in Fourier space which are used as points for averaging the acquired magnetic resonance data 142 and the simulated magnetic resonance data 146.

The computer storage 136 is further shown as containing corrected magnetic resonance data 148 which is calculated from the acquired magnetic resonance data 142 using the simulated magnetic resonance data 146 in order to determine a phase correction factor for the acquired magnetic resonance data 142. Finally, the computer storage 136 is shown as containing a diagnostic magnetic resonance image 150 which is reconstructed using the corrected magnetic resonance data 148. The diagnostic magnetic resonance image 150 may e.g. be reconstructed based on a parallel imaging magnetic resonance technique using the corrected magnetic resonance data 148. Depending on the parallel imaging magnetic resonance technique used for reconstructing the diagnostic magnetic resonance image 150 e.g. a set of coil sensitivities of antenna elements 126 may be used.

In some examples, the body coil 114 is not present. In other examples, the body coil 114 is used to acquire part of the magnetic resonance data 142.

The computer memory 138 is shown as being a control module 160. The control module 160 contains computer-executable code or instructions which enable the processor 133 to control the operation and function of the magnetic resonance imaging system. For instance, the control module 160 may work in conjunction with the pulse sequences 140 to acquire the various magnetic resonance data. The computer memory 138 is shown as further containing an imaging reconstruction Fourier transform module 162 and phase correction module 164. These two modules 162, 164 contain computer-executable code which enable the processor 133 to perform one or more of the methods shown in FIGS. 2 to 3. Furthermore, depending on the method used, the phase correction module 164 may also perform an averaging of magnetic resonance data 142, 146.

Figure 2:
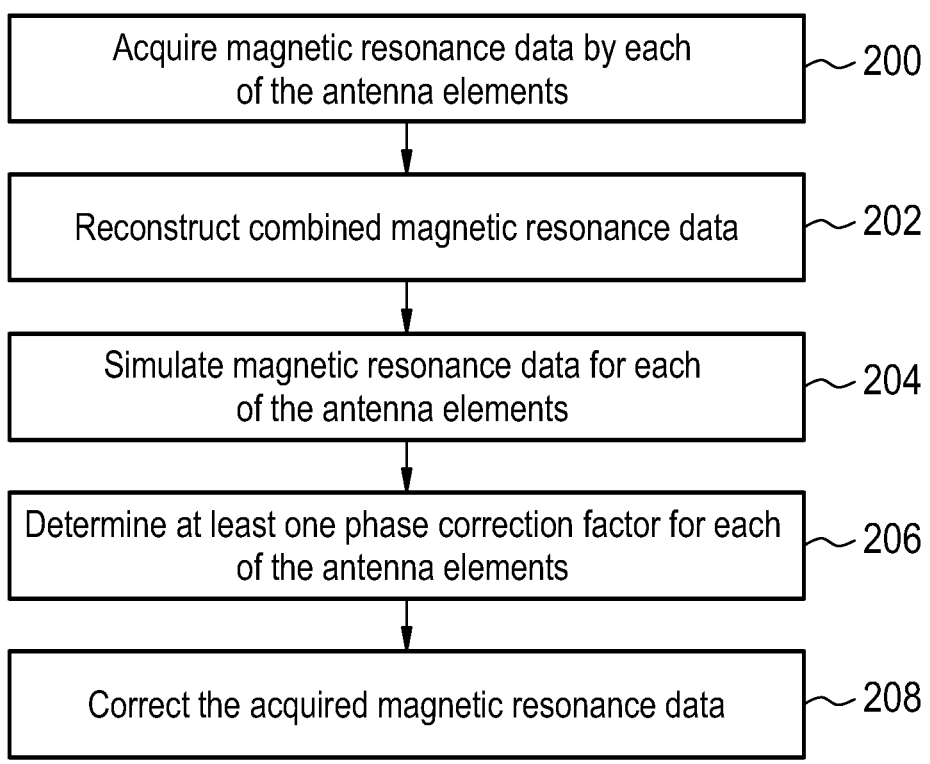
FIG. 2 illustrates an example of a method of operating the magnetic resonance imaging system of FIG. 1.

FIG. 2 shows a flowchart which illustrates a method of operating the magnetic resonance imaging system 100 shown in FIG. 1. In step 200, magnetic resonance data 142 is acquired from the imaging zone 108 by each of the antenna elements 126. For instance, the control module 160 may work in conjunction with the pulse sequences 140 to acquire the magnetic resonance data 142. Depending of the body coil 114, magnetic resonance data may also be acquired by the body coil, i.e. the body coil may may provide the functionality of an antenna element. In step 202, combined image data 144 is reconstructed from the magnetic resonance data 142. The acquired magnetic resonance data 142 of the antenna elements 126 is transformed from k-space to image space using inverse Fourier transformation. The transformation may be executed using the transformation module 162. The resulting image data of two or more of the antenna elements 126 in image space is combined in receive the combined image data 146. According to embodiments the resulting image data of all the antenna elements 126 is combined. For example, a 3D image is reconstructed. According to further example, one or more 2D images, e.g. a stack of 2D images, are reconstructed. For the reconstruction and or the combination of a parallel imaging protocol., like e.g. the SENSE protocol may be used. According to embodiments, multiple sets of magnetic resonace data 142 are acquired by each antenna element 126, each set of a given antenna element 126 being acquired at another time. The transformation may comprise averaging the acquired magnetic resonance data 142 of each antenna elements 126 over time, e.g. over the sets of magnetic resonace data 142 of the respective antenna element 126, and transforming the result from k-space to image space, or first transforming to image space followed by averaging over time.

In step 204, the magnetic resonance data acquired by each antenna element is simulated using the reconstructed combined image data 144. The reconstructed combined image data 144 is transformed by the transformation module 162 from image space to k-space using Fourier transformation. According to embodiments all dimensions of image space are transformed into k-space dimensions, i.e. a full basis change transforming all coordinates of k-space is perfumed. According to other embodiments, only a subset of coordinates of k-space is transformed, while the remaining coordinates of k-space are kept untransformed. Thus, the reconstructed combined image data 144 are transformed into a hybrid space, i.e. a space e.g. comprising at least one image space dimension and one or more k-space dimensions. The simulated magnetic resonance data 146 may be the result of one the above transformations.

In step 206, for each antenna element a phase correction factor is determined by the phase correction module 164. The determination comprises calculating phase differences between the acquired magnetic resonance data 142 and the simulated magnetic resonance data 146 of the respective antenna element. According to embodiments, the phase difference may calculated by computing the ratio of the acquired magnetic resonance data 142 and the simulated magnetic resonance data 146, e.g. for each data point in k-space or hybrid space. According to other embodiments the product of the acquired magnetic resonance data 142 and the complex conjugate of the simulated magnetic resonance data 146 is computed, e.g. for each data point in k-space or hybrid space. According to further embodiments, ratio or product is averaged. For example, the acquired magnetic resonance data 142 and the simulated magnetic resonance data 146 is averaged over the read-out direction, i.e. over $k_x$ in case of the full k-space or x in case of the hybrid space. According to other examples, it is averaged over channels, i.e. the magnetic resonance data 146 simulated for the different antenna elements 126 as well as the magnetic resonance data 142 acquired by the different antenna elements 126 is averaged over the antenna elements. According to further embodiments, it is averaged over time. Magnetic resonance data 142, 146 of k-space points for which the magnetic resonance data 142 has been acquired within a predefined time-window are averaged. According to embodiments, all the acquired magnetic resonance data 142 and the simulated magnetic resonance data 146 which is averaged may be weighted equally or the data points may be assigned with different weightening factors. For example, a Gaussian distribution of weighing factors may be assigned to the data points, when being averaged. A phase correction factor may be determined for each data point comprised by the acquired magnetic resonance data 142. However, averaging may result in equal phase correction factors for one or more of the dta points comprised by the acquired magnetic resonance data 142.

In step 208, the phase correction factor calculated in step 206 is used by the phase correction module 164 to correct the acquired magnetic resonance data 142 of each antenna element. Each data point comprised by the acquired magnetic resonance data 142 may be corrected using the phase correction factor calculated for the respective data point resulting in the corrected magnetic resonance data 148.

Figure 3:
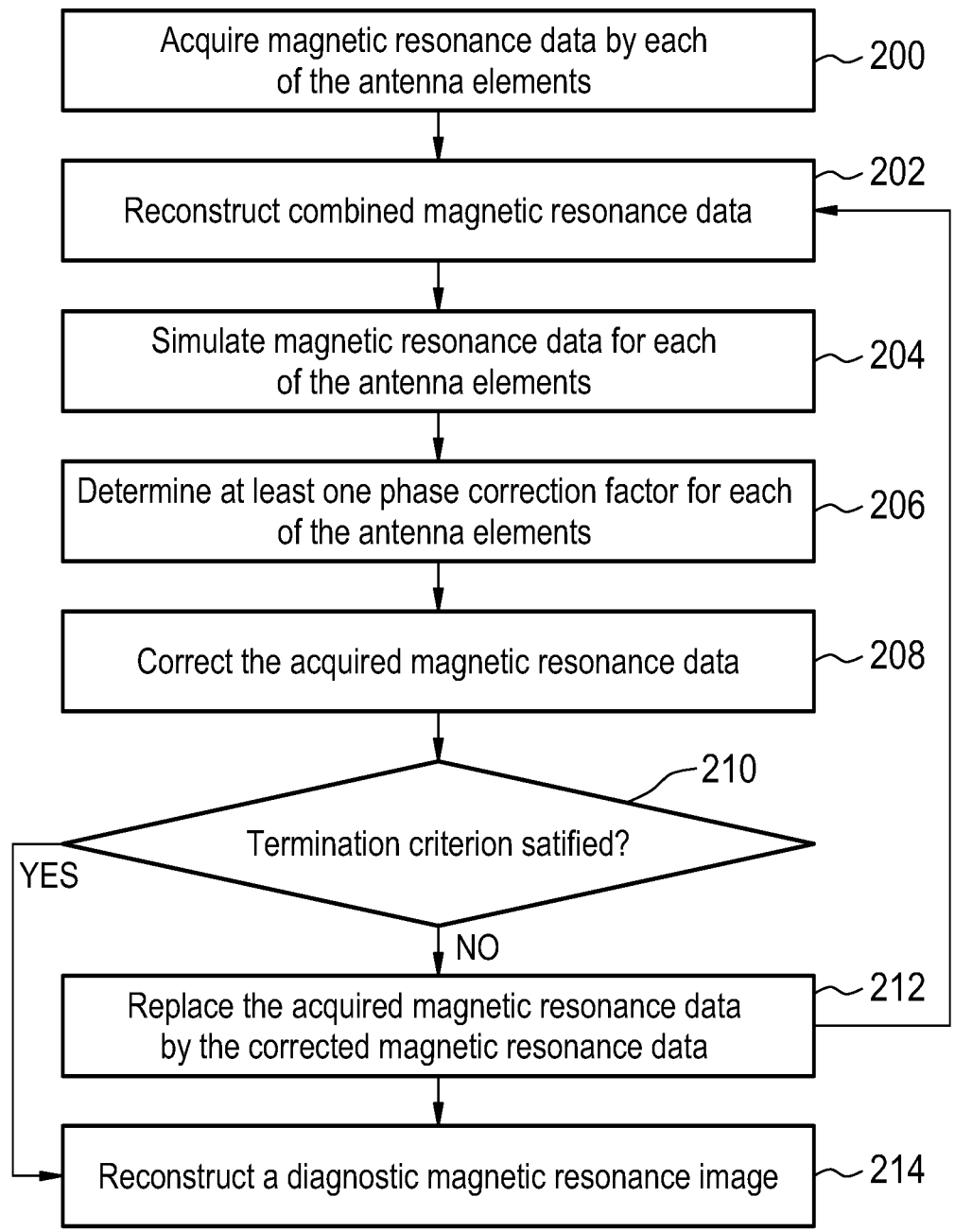
FIG. 3 further illustrates an iterative variant of the method illustrated in FIG. 2.

FIG. 3 shows a flowchart of an iterative implementation of the method of v 2. After the correction of the acquired magnetic resonance data 142, i.e. the calculation of the corrected magnetic resonance data 148, in step 210 it is checked whether a predefined termination criterion is satisfied. The termination criterion may e.g. require that the phase correction factor determined in step 206 is smaller than a predefined threshold or that a predefined maximum number of iteration steps is reached. In case the phase correction factor is not smaller than a predefined threshold, thus satisfying the termination criterion, the method is continued with step 212. In step 212, the acquired magnetic resonance data 142 is replaced by the corrected magnetic resonance data 146 for the further procedure. In other words, steps 201 to 208 of the method are repeated with the corrected magnetic resonance data 146 instead of the acquired magnetic resonance data 142. After the repetition, which results in new corrected magnetic resonance data, it is checked in step 210 for the new corrected magnetic resonance data, whether the termination criterion is satisfied, e.g. whether the phase correction factor determined by repeating steps 201 to 208 is smaller than the predefined threshold. Thus, the steps 202 to 208 are iteratively repeated until a correction factor is determined which is smaller than the predefined threshold. In case of a plurality of phase correction factors, where each phase correction factor is calculated foor ome of the data points comprised by the acquired magnetic resonance data 142, the steps 202 may be repeated until each of the phase correction factors are smaller than the threshold.

In case it is determined in step 210 that the termination criterion is satisfied, the method may be continued in step 214. In step 214 the correct magnetic resonance data last calculated is used to reconstruct a diagnostic magnetic resonance image 150. The diagnostic magnetic resonance image 150 may be reconstructed from the corrected magnetic resonance data last calculated using a parallel imagine protocol, like e.g. the SENSE protocol.

Figure 4:
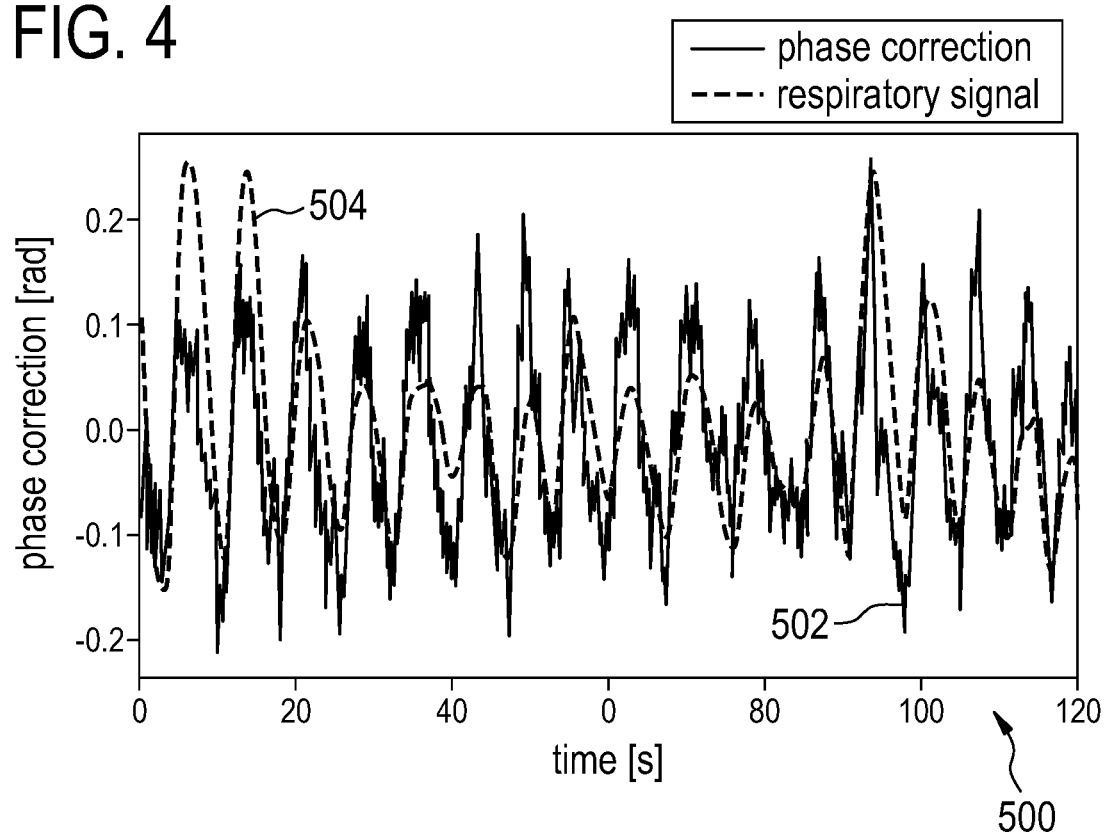
FIG. 4 illustrates the phase correction in relation to a respiratory motion $B_0$-fluctuations.

FIG. 4 shows a diagram 500 which illustrates the correlation of the estimated phase correction 502 with the signal of a respiratory bellows 504, i.e. the breathing motion of a subject. Physiologic sources, like e.g. a breathing motion, may introduce drifts or fluctuations of the main magnetic filed, i.e. the $B_0$-off-resonance field, which may have a significant impact on image quality. They may e.g. lead to ghosting and other artefacts. As shown in diagram 500, the phase correction factor 502 determined by the method of FIGS. 2 and 3 in case of an main magnetic felad which comprises inhomogeneties induced by breathing motions of the subject, may correspond to the respective breathing motion 504. Therefore, phase artefacts induced by breathing motion may efficiently be corrected using the data-driven correction method described above e.g. with regard of FIGS. 2 and 3.

Figure 5A:
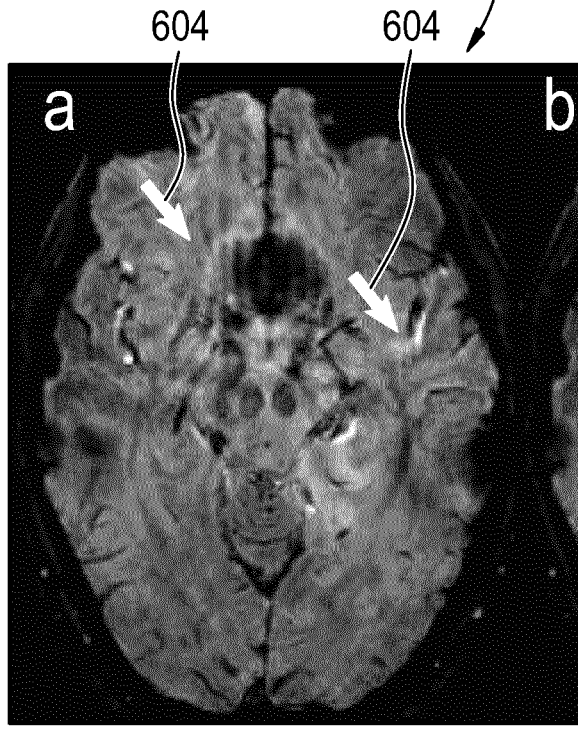
FIGS. 5A and 5B illustrate artifacts which may be induced by $B_0$-fluctuations.
Figure 5B:
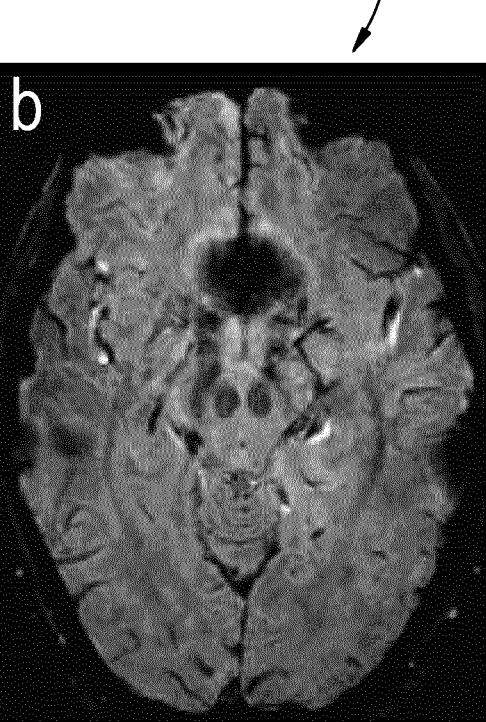

FIGS. 5A and 5B show the impact on the estimated phase correction on a $T_2^*$-weighted, gradient-echo brain image. FIG. 5A shows an uncorrected magnitude brain image 600 at TE=26.6 ms. FIG. 5B shows a corrected magnitude brain image 602 at TE=26.6 ms. In other words, FIG. 5A shows a diagnostic magnetic resonance image which has been reconstructed using the uncorrected magnetic resonance data acquired by the antenna elements. FIG. 5B shows a diagnostic magnetic resonance image which has been recontructed using the corrected magnetic resonance data calculated according to one or more of the aforementioned embodiments. Artifacts due to $B_0$-fluctuation are present in FIG. 5A as medium range ripples and intensity modulations, some of which are marked by arrows 604. These artefacts can be efficiently corrected using the data-driven approach for correcting phase depending artefacts as described above. This can be seen from the corrected image 602 shown of FIG. 5B in which the artefacts 604 indicated in the uncorrected image 600 are absent.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 main magnet
106 bore of magnet
108 imaging zone
110 magnetic field gradient coils
112 magnetic field gradient coil power supply
114 body coil
116 transceiver
118 subject
120 subject support
122 transceiver
124 magnetic resonance image coil
126 antenna element
130 computer
132 hardware interface
134 user interface
136 computer storage
138 computer memory
140 pulse sequences
142 acquired magnetic resonance data
144 reconstructed combined image data
146 simulated magnetic resonance data
148 corrected magnetic resonance data
150 diagnostic magnetic resonance image
160 control module
162 image reconstruction and Fourier transform module
164 phase correction module
500 diagram
502 phase correction
504 respiratory signal
600 uncorrected brain image
602 corrected brain image
604 artifact

The invention claimed is:

1. A magnetic resonance imaging system comprising:
a main magnet for generating a main magnetic field within an imaging zone,
a magnetic field gradient system for generating a spatially dependent gradient magnetic field within the imaging zone,
a radio-frequency system comprising a set of antenna elements each configured for acquiring magnetic resonance data from the imaging zone, a memory storing machine executable instructions and pulse sequence commands, wherein the pulse sequence commands are configured for controlling the magnetic resonance imaging system to acquire the magnetic resonance data from the imaging zone, a processor for controlling the magnetic resonance imaging system, wherein execution of the machine executable instructions causes the processor to control the magnetic resonance imaging system to:

acquire magnetic resonance data from the imaging zone by each of the antenna elements, reconstruct combined image data, wherein the reconstruction comprises transforming the acquired magnetic resonance data of the antenna elements from k-space to image space and combining the resulting image data of the antenna elements using the respective antenna elements' sensitivities, simulate magnetic resonance data acquired by each antenna element using the reconstructed combined image data, wherein the simulation comprises transforming the reconstructed combined image data from image space to k-space, determine for each antenna element a phase correction factor for the acquired magnetic resonance data of the respective antenna element, wherein the determination comprises calculating phase differences between the acquired magnetic resonance data and the simulated magnetic resonance data of the respective antenna element, correct the acquired magnetic resonance data of each antenna element using the phase correction factor determined for the respective antenna element.

2. The magnetic resonance imaging system of claim 1, wherein the reconstruction of combined image data, the simulation of magnetic resonance data, the determination of the phase correction factor and the correction of the acquired magnetic resonance data are iteratively repeated using the corrected magnetic resonance data in order to further correct the corrected magnetic resonance data until a predefined termination criterion is satisfied.

3. The magnetic resonance imaging system of claim 1, wherein each antenna element acquires multiple sets of magnetic resonance data from the imaging zone, wherein each one of the sets is acquired at a different time, wherein the transformation of the acquired magnetic resonance data of the antenna elements from k-space to image space comprises:

for each antenna element averaging the acquired magnetic resonance data of the sets of the respective antenna element over time and transforming the resulting magnetic resonance data from k-space to image space or for each antenna element transforming the magnetic resonance data of the sets of the respective antenna element from k-space to image space and averaging the resulting magnetic resonance data over time.

4. The magnetic resonance imaging system of claim 1, wherein for each point in k-space comprised by the acquired magnetic resonance data an individual phase correction factor is determined and used for the correction of the magnetic resonance data acquired for the respective point, wherein the determination of the individual phase correction factors comprises calculating for each of the points in k-space an individual phase difference between the magnetic resonance data acquired for the respective point and the magnetic resonance data simulated for the respective point.

5. The magnetic resonance imaging system of claim 1, wherein the phase correction factor is an averaged phase correction factor determined for a subset of the acquired magnetic resonance data and used for the correction of the acquired magnetic resonance data comprised by the subset, wherein the determination of the averaged phase correction factor comprises calculating an averaged phase difference by averaging over the phase differences calculated between the acquired magnetic resonance data comprised by the subset and the simulated magnetic resonance data.

6. The magnetic resonance imaging system of claim 5, wherein the subset comprises a first data selection of the acquired magnetic resonance data which is located on a line along a read-out direction in k-space such that the averaged phase difference is averaged over the read-out direction.

7. The magnetic resonance imaging system of claim 5, wherein the subset comprises a second data selection of the acquired magnetic resonance data of different ones of the antenna elements acquired for the same point in k-space such that the averaged phase difference is averaged over antenna elements.

8. The magnetic resonance imaging system of claim 5, wherein the subset comprises a third data selection of the acquired magnetic resonance data which is acquired within a predefined time window such that the averaged phase difference is averaged over the time window.

9. The magnetic resonance imaging system of claim 5, wherein weighting factors are assigned to the acquired magnetic resonance data comprised by the subset and used for calculating the averaged phase difference.

10. The magnetic resonance imaging system of claim 1, wherein the transformation of the reconstructed combined image data from image space to k-space is performed for each dimension of image-space.

11. The magnetic resonance imaging system of claim 1, wherein the transformation of the reconstructed combined image data from image space to k-space is performed for each dimension of image-space except for a subset of dimensions of the image space which are kept untransformed such that the resulting simulated magnetic resonance data is located in a hybrid space comprising the subset of dimensions of image space and one or more k-space dimensions, and wherein for the determination of the phase correction factor and the correction of the acquired magnetic resonance data a transformation of the acquired magnetic resonance data of each antenna element from k-space to image space is performed for the subset of dimensions of image space such that the resulting transformed acquired magnetic resonance data is located in the hybrid space and the determination of the phase correction factor and the correction of the acquired magnetic resonance data are performed in the hybrid space using the transformed acquired magnetic resonance data.

12. The magnetic resonance imaging system of claim 1, wherein an interlaced sampling scheme in k-space is used for the acquisition of the magnetic resonance data, wherein according to the interlaced sampling scheme magnetic resonance data from neighboring points in k-space comprised by the acquired magnetic resonance data is not acquired in direct succession.

13. A computer program product comprising machine executable instructions stored on a non-transitory computer readable medium for execution by a processor controlling a magnetic resonance imaging system, wherein the magnetic resonance imaging system comprises:
- a main magnet for generating a main magnetic field within an imaging zone,
- a magnetic field gradient system for generating a spatially dependent gradient magnetic field within the imaging zone,
- a radio-frequency system comprising a plurality of antenna elements each configured for acquiring magnetic resonance data from the imaging zone,
- a memory for storing the machine executable instructions and pulse sequence commands, wherein the pulse sequence commands are configured for controlling the magnetic resonance imaging system to acquire the magnetic resonance data from the imaging zone,
- wherein execution of the machine executable instructions causes the processor to control the magnetic resonance imaging system to:
- acquire magnetic resonance data from the imaging zone by each of the antenna elements,
  - reconstruct combined image data, wherein the reconstruction comprises transforming the acquired magnetic resonance data of the antenna elements from k-space to image space and combining the resulting image data of the antenna elements using the respective antenna elements' sensitivities,
  - simulate magnetic resonance data acquired by each antenna element using the reconstructed combined image data, wherein the simulation comprises transforming the reconstructed combined image data from image space to k-space,
  - determine for each antenna element a phase correction factor for the acquired magnetic resonance data of the respective antenna element, wherein the determination comprises calculating phase differences between the acquired magnetic resonance data and the simulated magnetic resonance data of the respective antenna element,
  - correct the acquired magnetic resonance data of each antenna element using the phase correction factor determined for the respective antenna element.

14. A method of operating a magnetic resonance imaging system, wherein the magnetic resonance imaging system comprises:
- a main magnet for generating a main magnetic field within an imaging zone,
- a magnetic field gradient system for generating a spatially dependent gradient magnetic field within the imaging zone,
- a radio-frequency system comprising a plurality of antenna elements each configured for acquiring magnetic resonance data from the imaging zone,
- a memory storing machine executable instructions and pulse sequence commands, wherein the pulse sequence commands are configured for controlling the magnetic resonance imaging system to acquire the magnetic resonance data from the imaging zone, wherein the method comprises:
  - acquiring magnetic resonance data from the imaging zone by each of the antenna elements,
  - reconstructing combined image data, wherein the reconstruction comprises transforming the acquired magnetic resonance data of the antenna elements from k-space to image space and combining the resulting image data of the antenna elements using the respective antenna elements' sensitivities,
  - simulating magnetic resonance data acquired by each antenna element using the reconstructed combined image data, wherein the simulation comprises transforming the reconstructed combined image data from image space to k-space,
  - determining for each antenna element a phase correction factor for the acquired magnetic resonance data of the respective antenna element, wherein the determination comprises calculating phase differences between the acquired magnetic resonance data and the simulated magnetic resonance data of the respective antenna element,
  - correcting the acquired magnetic resonance data of each antenna element using the phase correction factor determined for the respective antenna element.

* * * * *